US012171995B1

(12) United States Patent
Reid et al.

(10) Patent No.: US 12,171,995 B1
(45) Date of Patent: Dec. 24, 2024

(54) METHODS FOR IMPROVED BIOCOMPATIBILITY FOR HUMAN IMPLANTED MEDICAL DEVICES

(71) Applicant: PARADROMICS, INC., Austin, TX (US)

(72) Inventors: Kimberly G. Reid, Austin, TX (US); Kunal Sahasrabuddhe, Austin, TX (US); Aleksandar Tadic, Austin, TX (US); Yifan Kong, Austin, TX (US); Michael E. Landry, Austin, TX (US)

(73) Assignee: Paradromics, Inc., Austin, TX (US)

( * ) Notice: Subject to any disclaimer, the term of this patent is extended or adjusted under 35 U.S.C. 154(b) by 146 days.

(21) Appl. No.: 17/937,374

(22) Filed: Sep. 30, 2022

Related U.S. Application Data

(60) Provisional application No. 63/253,295, filed on Oct. 7, 2021.

(51) Int. Cl.
*C23C 16/455* (2006.01)
*A61N 1/04* (2006.01)
*C23C 16/34* (2006.01)

(52) U.S. Cl.
CPC .............. *A61N 1/042* (2013.01); *C23C 16/34* (2013.01); *C23C 16/45525* (2013.01); *A61B 2562/125* (2013.01)

(58) Field of Classification Search
CPC .............. C23C 16/45525; C23C 16/34; A61B 2562/125
See application file for complete search history.

(56) References Cited

U.S. PATENT DOCUMENTS

| | | |
|---|---|---|
| 3,982,529 A | 9/1976 | Sato |
| 5,008,733 A | 4/1991 | Mine et al. |
| 5,721,450 A | 2/1998 | Miles |
| 5,814,122 A | 9/1998 | Huang |
| 6,049,038 A | 4/2000 | Suzuki |
| 6,156,978 A | 12/2000 | Peck et al. |
| 6,249,965 B1 | 6/2001 | Bullara et al. |
| 6,393,327 B1 | 5/2002 | Scribner |

(Continued)

FOREIGN PATENT DOCUMENTS

| | | |
|---|---|---|
| EP | 2495011 A1 | 9/2012 |
| WO | WO-2017180482 A1 | 10/2017 |

(Continued)

OTHER PUBLICATIONS

Li, Changzheng, et al., "Ultra-Long-Term Reliable Encapsulation Using an Atomic Layer Deposited HfO2/Al2O3/HfO2 Triple-Interlayer for Biomedical Implants". Coatings 2019, 9, 579, pp. 1-13.*

(Continued)

*Primary Examiner* — Bret P Chen
(74) *Attorney, Agent, or Firm* — Wilson Sonsini Goodrich & Rosati (57) ABSTRACT

Described herein are methods for generating a coated device, electrode, or portion of an electrode for implanting into a subject. Such devices and electrodes are generated using methods like atomic layer deposition. In some cases, methods like etching are used to expose portions of a coated surface. The methods described herein improve overall hermeticity, biocompatibility, and biostability of implantable devices.

20 Claims, 4 Drawing Sheets

(56) References Cited

U.S. PATENT DOCUMENTS

| | | | |
|---|---|---|---|
| 6,647,297 | B2 | 11/2003 | Scribner et al. |
| 6,815,258 | B2 | 11/2004 | Vincent |
| 6,920,359 | B2 | 7/2005 | Meadows et al. |
| 6,940,182 | B2 | 9/2005 | Hilton et al. |
| 7,091,060 | B2 | 8/2006 | Bolken et al. |
| 7,134,198 | B2 | 11/2006 | Nakatani et al. |
| 7,306,976 | B2 | 12/2007 | Feustel et al. |
| 7,991,475 | B1 | 8/2011 | Tang et al. |
| 8,010,208 | B2 | 8/2011 | Nimer, II et al. |
| 8,024,049 | B1 | 9/2011 | Gilson et al. |
| 8,280,516 | B2 | 10/2012 | Graupe |
| 8,406,889 | B2 | 3/2013 | Llinas et al. |
| 8,412,332 | B2 | 4/2013 | Massoud-Ansari et al. |
| 8,649,873 | B2 | 2/2014 | Moffitt et al. |
| 8,798,737 | B2 | 8/2014 | Merz et al. |
| 8,849,408 | B1 | 9/2014 | Gilson et al. |
| 8,929,992 | B2 | 1/2015 | Toader et al. |
| 8,944,985 | B2 | 2/2015 | Bonmassar et al. |
| 8,991,680 | B1 | 3/2015 | Schulman et al. |
| 10,327,655 | B2 | 6/2019 | Angle et al. |
| 10,390,724 | B2 | 8/2019 | Fonash et al. |
| 10,564,208 | B1 | 2/2020 | Angle et al. |
| 10,653,330 | B2 | 5/2020 | Angle et al. |
| 11,071,465 | B2 | 7/2021 | Angle et al. |
| 11,395,924 | B2 | 7/2022 | McLaughlin et al. |
| 11,401,620 | B2 | 8/2022 | Kong et al. |
| 2002/0014688 | A1 | 2/2002 | Ramalingam et al. |
| 2003/0100823 | A1 | 5/2003 | Kipke et al. |
| 2004/0006264 | A1 | 1/2004 | Mojarradi et al. |
| 2004/0026792 | A1 | 2/2004 | Vincent |
| 2004/0133118 | A1 | 7/2004 | Llinas |
| 2004/0222010 | A1 | 11/2004 | Tonucci et al. |
| 2005/0217796 | A1 | 10/2005 | Carter et al. |
| 2005/0267347 | A1 | 12/2005 | Oster |
| 2006/0172179 | A1* | 8/2006 | Gu .................. H01M 4/8892 252/502 |
| 2006/0206161 | A1 | 9/2006 | Nicolelis et al. |
| 2006/0265039 | A1 | 11/2006 | Bartic et al. |
| 2007/0106143 | A1 | 5/2007 | Flaherty |
| 2007/0142872 | A1 | 6/2007 | Mickle et al. |
| 2007/0250142 | A1* | 10/2007 | Francis ................ A61L 31/082 607/116 |
| 2008/0140159 | A1* | 6/2008 | Bornhoft ............ A61B 5/0006 607/60 |
| 2008/0170819 | A1 | 7/2008 | Kodama et al. |
| 2008/0205829 | A1 | 8/2008 | Jacobsen et al. |
| 2008/0208283 | A1 | 8/2008 | Vetter et al. |
| 2009/0004471 | A1 | 1/2009 | Amthor |
| 2009/0069706 | A1 | 3/2009 | Boogaard et al. |
| 2009/0120216 | A1 | 5/2009 | Chiou et al. |
| 2009/0304774 | A1* | 12/2009 | Liang .................. C12N 11/14 623/23.72 |
| 2010/0016928 | A1* | 1/2010 | Zdeblick ................ H01L 24/63 607/72 |
| 2010/0029148 | A1 | 2/2010 | Perlin et al. |
| 2010/0069776 | A1 | 3/2010 | Greger et al. |
| 2010/0114272 | A1 | 5/2010 | Haidarliu et al. |
| 2010/0161019 | A1 | 6/2010 | Clark et al. |
| 2011/0208031 | A1 | 8/2011 | Wolfe et al. |
| 2012/0041294 | A1 | 2/2012 | Bai |
| 2012/0109262 | A1 | 5/2012 | Martens et al. |
| 2012/0279852 | A1 | 11/2012 | Zach |
| 2013/0030500 | A1 | 1/2013 | Toader et al. |
| 2013/0175733 | A1 | 7/2013 | De Volder et al. |
| 2013/0190586 | A1 | 7/2013 | Akingba et al. |
| 2013/0190851 | A1* | 7/2013 | Schouenborg ....... A61N 1/0536 607/116 |
| 2013/0274843 | A1 | 10/2013 | Barker et al. |
| 2013/0337583 | A1* | 12/2013 | Kobayashi ........ H01L 21/76825 438/4 |
| 2014/0107728 | A1 | 4/2014 | Fried et al. |
| 2014/0309548 | A1 | 10/2014 | Merz et al. |
| 2014/0330354 | A1 | 11/2014 | Shelton et al. |
| 2014/0350634 | A1 | 11/2014 | Grill et al. |
| 2015/0065831 | A1 | 3/2015 | Popovic et al. |
| 2015/0368822 | A1* | 12/2015 | Sammelselg ........ C25D 11/024 428/312.8 |
| 2016/0029998 | A1* | 2/2016 | Brister .................. A61B 8/0833 600/424 |
| 2016/0049293 | A1* | 2/2016 | Li ...................... H01L 21/02214 438/780 |
| 2016/0128588 | A1 | 5/2016 | Melosh et al. |
| 2016/0235967 | A1 | 8/2016 | Shan et al. |
| 2016/0302687 | A1 | 10/2016 | Lee et al. |
| 2017/0007813 | A1 | 1/2017 | Negi et al. |
| 2017/0290521 | A1* | 10/2017 | Angle .................. A61B 5/6868 |
| 2017/0358488 | A1* | 12/2017 | Cho .................. H01L 21/76829 |
| 2018/0085018 | A1 | 3/2018 | Angle et al. |
| 2018/0221663 | A1 | 8/2018 | Saini |
| 2019/0246929 | A1 | 8/2019 | Angle et al. |
| 2020/0046240 | A1 | 2/2020 | Angle et al. |
| 2020/0215335 | A1 | 7/2020 | McLaughlin et al. |
| 2021/0098341 | A1 | 4/2021 | Kong et al. |
| 2021/0310988 | A1* | 10/2021 | McGrath .............. C12Q 1/6806 |
| 2021/0378526 | A1 | 12/2021 | Angle et al. |
| 2022/0110681 | A1 | 4/2022 | Angle et al. |
| 2022/0175320 | A1 | 6/2022 | Shah et al. |

FOREIGN PATENT DOCUMENTS

| | | |
|---|---|---|
| WO | WO-2018039648 A1 | 3/2018 |
| WO | WO-2018057667 A1 | 3/2018 |
| WO | WO-2018183967 A1 | 10/2018 |
| WO | WO-2018191725 A1 | 10/2018 |
| WO | WO-2020180696 A1 | 9/2020 |

OTHER PUBLICATIONS

Ghelich, Pejman, et al., "Unprotected sidewalls of implantable silicon-based neural probes and conformal coating as a solution". Npj Mater Degrad. 2021; 5, pp. 1-16.*

Astaneh, Sarah Hashemi, et al., "Atomic layer deposition on dental materials: Processing conditions and surface functionalization to improve physical, chemical, and clinical properties—A review". Acta Biomaterialia 121 (2021) 103-118.*

Blomberg, Tom, et al., "Atomic Layer Deposition Coatings for Medical Devices". ECS Meeting Abstracts, vol. MA2019-02, G02—Atomic Layer Deposition Applications 15, 1126. 4 pages. Abstact Only.*

Applied Materials brochure, "Enabling Next Generation Electronic Medical Devices With Atomic Layer Deposition". 9 pages. No Date or Author Available.*

Goto, Kazuya, et al., "Transcutaneous photocoupler for transmission of biological signals". Optics Letters, vol. 27, No. 20, Oct. 15, 2002, pp. 1797-1799.*

Webb, James Luke, et al., "Detection of biological signals from a live mammalian muscle using an early stage diamond quantum sensor". Scientific Reports (2021) 11:2412, pp. 1-11.*

Angle et al. Neuronal Recordings with Solid-Conductor Intracellular Nanoelectrodes (SCINEs). PLOS One 7(8):E43194 (Aug. 2012). 8 pages.

Bouton, C. et al., Restoring cortical control of functional movement in a human with quadriplegia. Nature (2016). 13 pages. Retrieved Feb. 15, 2023 at URL: https://www.researchgate.net/profile/Marcia-Bockbrader/publication/301247939_Restoring_cortical_control_of_functional_movement_in_a_human_with_quadriplegia/links/59d70c77a6fdcc52acaa0075/Restoring-cortical-control-of-functional-movement-in-a-human-with-quadriplegia.pdf.

Brenner, W. Use underfill encapsulants to enhance flip-chip assembly reliability. Electronic Design. Jul. 30, 2012; Retrieved Feb. 29, 2016 available at http://electronicdesign.com/boards/useunderfillencapsulantsenhanceflipchipassemblyreliability.

Co-pending U.S. Appl. No. 16/058,966, inventors Angle; Matthew R. et al., filed on Aug. 8, 2018.

Co-pending U.S. Appl. No. 16/276,503, inventors Angle; Matthew et al., filed on Feb. 14, 2019.

Co-pending U.S. Appl. No. 16/807,042, inventors Angle; Matthew et al., filed on Mar. 2, 2020.

(56) References Cited

OTHER PUBLICATIONS

Co-pending U.S. Appl. No. 17/856,843, inventors Angle; Matthew et al., filed on Jul. 1, 2022.
Co-pending U.S. Appl. No. 18/053,106, inventors Angle; Matthew et al., filed on Nov. 7, 2022.
Co-pending U.S. Appl. No. 18/105,591, inventors Boergens; Kevin et al., filed on Feb. 3, 2023.
Co-pending U.S. Appl. No. 18/177,024, inventors Landry; Michael et al., filed on Mar. 1, 2023.
Hajjhassan et al. NeuroMEMS: Neural Probe Microtechnologies. Sensors 8(10):6704-6726 (Oct. 25, 2008). doi: https://doi.org/10.3390/s8106704 .
Instruction for use (IFU) Blackrock research assemblies. Blackrock Microsystems, LLC. 2014. pp. 0-13.
International Search Report dated Jun. 19, 2017 for International Application No. PCT/US2017/026707.
Johnson, L.J. et al., A novel high electrode count spike recording array using an 81,920 pixel transimpedance amplifier-based imaging chip. Journal of Neuroscience methods. 205; 2012: 223-232.
Johnson, R. Wayne, Chapter 19: Flip Chip Assembly and underfilling, Auburn University (2001). Available at https://pdfs.semanticscholar.org/3c24/524ef9ede82c95ba10caae142e3ca8b58966.pdf.
Liao et al. Fabrication of high aspect ratio microstructure arrays by micro reverse wire—EDM. J. Micromech. Microeng. 15 (2005) 1547-1555.
Mauron, F. Improvements in glass encapsulation technology offer significant advantages for implantable medical devices. Valtronic. p. 1-10. Jul. 2013. Retrieved Mar. 2, 2023 at URL: http://www.implantable-device.com/wp-content/uploads/2013/07/Valtronic-Glass-Encapsulation-White-Paper.pdf.
Office Action dated Jun. 30, 2017 for U.S. Appl. No. 15/482,583.
Office Action dated Nov. 28, 2017 for U.S. Appl. No. 15/482,583.
PCT/US2018/025576 International Search Report and Written Opinion dated Jul. 30, 2018.
Scribner, D. et al., A retinal prosthesis technology based on CMOS microelectronics and microwire glass electrodes. IEEE transactions on biomedical circuits and systems, 1(1); Mar. 2007: p. 73-84.
U.S. Appl. No. 15/482,583 Notice of Allowance dated Mar. 6, 2019.
U.S. Appl. No. 16/584,630 Notice of Allowance dated Apr. 27, 2022.
U.S. Appl. No. 16/584,630 Notice of Allowance dated May 26, 2022.
U.S. Appl. No. 15/482,583 Office Action dated Aug. 28, 2018.
U.S. Appl. No. 15/482,583 Notice of Allowance dated Apr. 23, 2019.
U.S. Appl. No. 15/482,583 Notice of Allowance dated Mar. 20, 2019.
U.S. Appl. No. 16/584,630 Office Action dated Mar. 1, 2022.
Bashkatov et al. Optical Properties of the Subcutaneous Adipose Tissue in the Spectral Range 400-2500 nm. Optics and Spectroscopy, vol. 99, No. 5, 2005, pp. 836-842.
Co-pending U.S. Appl. No. 18/184,572, inventors Burrows; James et al., filed on Mar. 15, 2023.
Co-pending U.S. Appl. No. 18/316,127, inventor Burrows; James, filed on May 11, 2023.
Co-pending U.S. Appl. No. 18/329,485, inventors Angle; Matthew et al., filed on Jun. 5, 2023.
Co-pending U.S. Appl. No. 18/342,602, inventors Angle; Matthew et al., filed on Jun. 27, 2023.
Stolp et al. Immune responses at brain barriers and implications for brain development and neurological function in later life. Frontiers in Integrative Neuroscience, vol. 7, Article 61 (Aug. 23, 2013). 14 pages.
U.S. Appl. No. 17/031,584 Office Action dated Apr. 18, 2023.
Co-pending U.S. Appl. No. 18/806,233, inventors Landry; Michael E. et al., filed Aug. 15, 2024.
Co-pending U.S. Appl. No. 18/934,011, inventors Angle; Matthew et al., filed Oct. 31, 2024.

* cited by examiner

METHODS FOR IMPROVED BIOCOMPATIBILITY FOR HUMAN IMPLANTED MEDICAL DEVICES

CROSS-REFERENCE TO RELATED APPLICATIONS

This application claims the benefit of U.S. Provisional Application No. 63/253,295, filed Oct. 7, 2021, which application is incorporated herein by reference.

BACKGROUND OF THE INVENTION

Hermiticity, biocompatibility, and biostability are critical parameters for devices implanted in the human body. Hermiticity can be improved using thin film layers and nanolaminates deposited by methods such as atomic layer deposition (ALD), chemical vapor deposition (CVD), laser assisted deposition among others, by sealing microcracks or pores that allow molecules from a test environment to leak into components of the implanted device. Such thin film layers, or coatings, are generated using carefully selected materials in order to sustain biocompatibility and biostability once the device has been implanted in the human body.

SUMMARY OF THE INVENTION

The methods disclosed herein may be used to improve hermiticity, biocompatibility, and biostability in devices implanted in the human body. It is advantageous to have a deposition method which can provide a means to coat the device partially, or in full, with a uniform layer of a biostable material, while maintaining conductive properties. However, certain methods include implanting an exposed electrode or device in a subject which can result in fluid or material entering into sensitive components of a device. Accordingly, recognized herein is a need to address the aforementioned problem. Provided herein are methods that can provide a hermetically sealed device, including an electrode, for implanting into a subject which can improve overall biostability and biocompatibility of the device.

In one aspect, described herein is a method comprising: (a) providing a device that is (i) implantable in a tissue region of a subject and (ii) configured to detect or measure one or more biological signals from the tissue region; (b) applying one or more coatings to the device using at least atomic layer deposition to (i) seal one or more microcracks or pores in at least a portion of the device or (ii) reduce a size of the one or more microcracks or pores, thereby enhancing the hermeticity of the device; and (c) implanting the device in the tissue region of the subject to detect or measure the one or more biological signals of the subject.

In some embodiments, one or more coatings comprise a coating that (i) modifies one or more material properties of the device or (ii) provides a desired set of material properties for the device. In some embodiments, the one or more material properties and/or the desired set of material properties comprise hermeticity, one or more electrical properties (e.g., conductivity, resistivity, capacitance, or inductance), biocompatibility, or biostability of the device. In some embodiments, one or more material properties and/or the desired set of material properties comprise a shape, a texture, or a surface characteristic of the device or a portion thereof.

In some embodiments, at least a portion of the device comprises (i) one or more electronic components or circuits for processing the one or more biological signals, or (ii) an inner or outer portion of a housing of the device, which housing contains the one or more electronic components or circuits for processing the one or more biological signals.

In some embodiments, at least a portion of the device comprises one or more conducting feedthroughs of the device or a sealing material surrounding one or more conductive wires of the device.

In some embodiments, wherein at least a portion of the device comprises one or more electrodes configured to transmit the one or more biological signals from the tissue region of the subject to one or more electronic components or circuits of the device. In some embodiments, one or more coatings comprise (i) a conductive coating directly applied to the one or more electrodes and (ii) an insulating coating applied on or to the conducting coating.

In some embodiments, the method further comprises, prior to (b), masking one or more select regions of the one or more electrodes.

In some embodiments, the method further comprises, subsequent to (b), exposing at least a portion of the one or more electrodes to enable detection and/or transmission of the one or more biological signals.

In some embodiments, exposing at least the portion of the one or more electrodes comprises ablating at least one coating of the one or more coatings. In some embodiments, one or more coatings comprise a coating that reflects or mitigates laser light to control (i) an absorption of laser energy or (ii) a thermal dissipation of absorbed laser energy for one or more select areas or regions of the one or more electrodes. In some embodiments, exposing at least the portion of the one or more electrodes comprises chemically etching at least one coating of the one or more coatings. In some embodiments, one or more coatings comprise a coating that acts as an etch stop layer to chemically resist etching in or near one or more select areas or regions of the one or more electrodes.

In some embodiments, at least one coating of the one or more coatings is hydrophobic.

In some embodiments, one or more coatings comprise a plurality of coatings that are applied using different deposition techniques. In some embodiments, the different deposition techniques are selected from the group consisting of chemical vapor deposition, physical vapor deposition, electroplating, plasma enhanced chemical vapor deposition, low pressure chemical vapor deposition, and atomic layer deposition.

In some embodiments, the one or more coatings may comprise metal oxides, metal nitrides, metal carbides, non-metallic films, and/or metal films or alloys such as Al2O3, ZnO, TiO2, SiO2, HfO2, ZrO2, TiN, TiON, Fe2O3, Ta2O5, TaN, Ti, Pt, Co, Cr, Mo, Ni, Li, Ir, Ta, Nb, Pd, Sn, Fe, NbO, NbO2, Nb2O5, W, WO3, AlN, TiN, WN, IrO2, WC, diamond like carbon, Calcium phosphate or Ca—P—O.

In some embodiments, the method comprises, in (b), applying the one or more coatings comprises applying a plurality of repeatable layers of a film material, a nanolaminate, or ternary layer materials to the device or a portion thereof. The ternary layer material may comprise, for example, any compound or composition that can be represented as $A_xB_yC_z$, where A, B, and C are derived from or associated with a compound or composition AC and/or BC. In some embodiments, A and/or B may comprise, for example, a metal, a metal alloy, and/or any non-metallic element or material. In some embodiments, C may comprise one or more oxides, nitrides, carbides, metals, or metal alloys. In some cases, the metal or metal alloy may comprise, for instance, platinum or platinum iridium. In some non-limiting embodiments, and by way of example only, the ternary layer material may comprise a combination of two binary oxides. In some non-limiting embodiments, and by way of example only, the ternary layer material may comprise $Al_xHf_yO_z$.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than" or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Provided herein are methods that may be used to coat implantable devices, partially or fully, which results in improved hermiticity, biocompatibility, and biostability for an implantable device. Hermiticity may be defined as a characteristic of an object, or a portion thereof, where the object is air-tight or liquid-tight. In such objects, no gas or liquid may escape from or enter into the object. Biocompatibility may be defined as a property, where an object, or a portion thereof, or a material is compatible with living tissue or fluids. For example, the object or material does not produce a toxic or immunological response when exposed to a tissue or biological fluids. Biostability may be defined as the ability of a material or object to maintain physical and chemical integrity upon implantation into a living tissue or fluid.

A method may comprise: (a) providing a device that is (i) implantable in a tissue region of a subject and (ii) configured to detect or measure one or more biological signals from a tissue region (b) applying one or more coatings to a device using at least atomic layer deposition to (i) seal one or more microcracks or pores in at least a portion of the device or (ii) reduce a size of the one or more microcracks or pores, thereby enhancing the hermiticity of the device; and (c) implanting a device in a tissue region of a subject to detect or measure one or more biological signals of a subject.

A tissue region in a subject may be nervous tissue (e.g. brain tissue, spinal cord tissue, or nerves), muscle tissue (e.g. cardiac muscle, smooth muscle, or skeletal muscle), epithelial tissue (e.g. the lining of GI tract organs and other hollow organs, or skin surface), or connective tissue (e.g. fat, padding tissue, bone tissue, or tendons). A subject may be a living organism or a non-living organism. A subject may be a human subject or an animal subject. Animal subjects may include rodents (e.g., mice, rats, rabbits, guinea pigs, gerbils, hamsters), simians (e.g., monkeys, chimpanzees, orangutans, gorillas, and humans), equines (e.g. horses), bovines (e.g., cows), canines (e.g., domestic dogs), felines (e.g., domestic cats), avines, insects, crustaceans, mollusks, or any other types of animals.

The implantable devices of the present disclosure may be implanted into a tissue region in a subject fully or partially. In some instances, a portion of a device like a probe, electrode, or wire may be implanted into a tissue region of a subject. In some instances, the device, or a portion thereof, can be mounted on and/or inserted into a subject. A target area may include any tissue region of the subject. The device, or portion thereof, may be a device that can be partially or fully inserted into a subject (or tissue within a subject) or may measure signals from an exterior portion of a sample or subject. The probe may be coupled to the live subjects (e.g., for in vivo signal detection and/or processing) while the subjects are freely moving, freely behaving, or are still. In some instances, the subject may be immobilized or a portion of the subject (e.g., the head) may be immobilized during signal measurements. The subject may be conscious or may be unconscious. In some embodiments, the subject may or may not be anesthetized.

Biological signals detected from a subject may be electroencephalography (EEG), electrocorticography (EcOG), local field potentials (LFP), Multi-unit activity (MUA), single unit activity, electromyography (EMG), electrooculography (EOG), Electroretinography (ERG), electrocardiogramlectroatriography (EAG), electroventriculography (EVG), intracardiac electrogram (EGM), electronystagmography (ENG), electroantennaography (EAG), electrocochleography (ECOG), electrogastrography (EGG), electrogastroenterography (EGEG), electroglottography (EGG), electropalatography (EPG), electroarteriography (EAG), electroblepharography (EBG), electrogermography (EDG), electrohysterography (EHG), electroneurongraphy (ENcG), electropneumography (EPG), electrospinography (ESG), electrovomerography (EVG), surface electromyogram (sEMG), galvanic skin response (GSR), respiration, or any other type of signal that can be measured from a subject.

The device, or a portion thereof may be coated using a deposition-type technique. Coatings can be applied as one or more layers. In some instances, at least 1 coating, 2 coatings, 3 coatings, 4 coatings, 5 coatings, 6 coatings, 7 coatings, 8 coatings, 9 coatings, 10 coatings, 11 coatings, 12 coatings, 13 coatings, 14 coatings, 15 coatings, 20 coatings, 30 coatings, 50 coatings, or more may be applied. Coatings may be applied using atomic layer deposition (ALD), plasma enhanced atomic layer deposition (PEALD), chemical vapor deposition (CVD), plasma enhanced chemical vapor deposition (PECVD), physical vapor deposition (PVD), electroplating, plasma enhanced CVD, low pressure CVD, spin coating, sputtering, molecular beam epitaxy (MBE), molecule layer deposition, Langmuir-Blodgett method, chemical solution deposition (CSD), chemical bath deposition (CBD), sol-gel method, dip coating, thermal evaporation, pulsed laser deposition, cathodic arc deposition, ion beam deposition, electrospray deposition, electroplating, metalorganic vapor phase epitaxy (MOVPE), metalorganic CVD, or any combination thereof. All coatings may be applied using the same method. In some instances, at least one coating is applied using a different method. In some instances, at least one of the coatings is applied using ALD. In some instances, at least one of the coatings is applied using ALD, followed by another method to increase the overall thickness of a coating.

Figure 1:
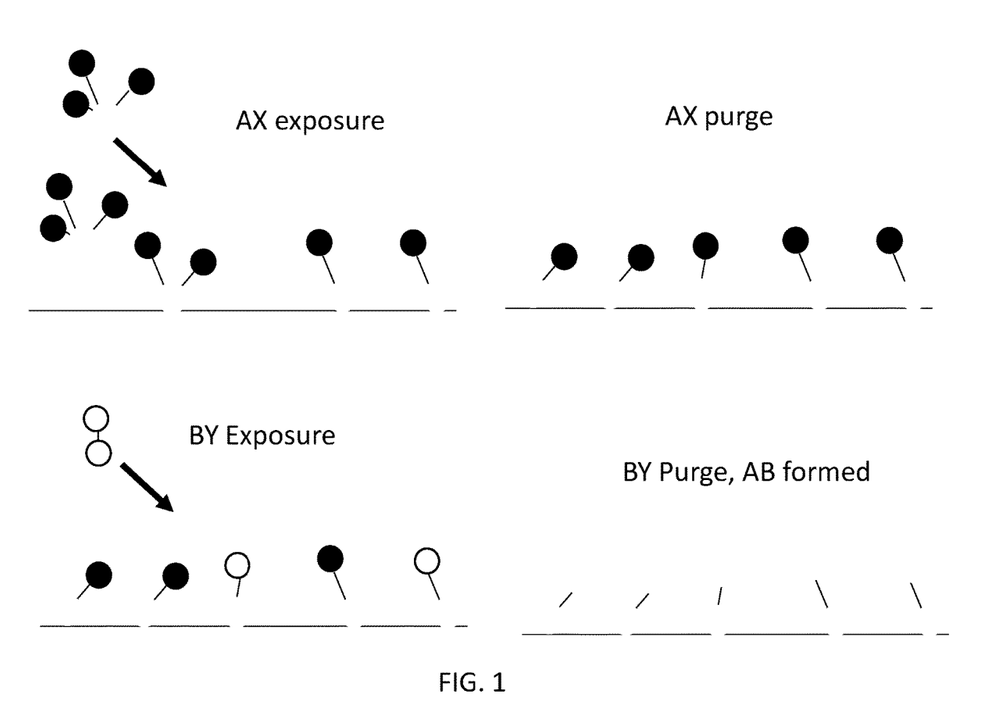
FIG. 1 illustrates the process of using atomic layer deposition (ALD) to coat a surface.

FIG. 1 illustrates an example process of using an ALD method to coat a surface. ALD is a unique surface reaction process which controls and allows a thin film to penetrate into nanopores and deposit as a film. ALD may effectively seal or reduce the size of an opening and pores. By the selection of reactants and deposition conditions, a self-limiting process results in the deposition of repeatable layers of film. One cycle is the exposure of a device or surface to a reactant, AX where X may represent an atomic or molecular ligand. In some instances, X may be more than one atom or more than one molecular ligand. In some embodiments, the chamber is purged and/or evacuated after exposure of AX. In some embodiments, a device or surface is exposed to reactant BY after purging and/or evacuating, where BY may be a molecule such as $H_2$, $NH_3$, $O_2$, $NH_3$, $O_3$, or any other molecule represented by BY described herein. AX and BY are chosen such that on a particular surface and at the chosen process conditions (temperature, pressure, gas flow, and exposure time) the ligands (i.e., X) of AX remain intact or partially intact such that the surface, or a portion thereof, is covered in a monolayer or sub-monolayer. In some aspects, AX may be chosen so that a surface, or portion thereof, is covered in one or more layers or sub-layers. In some aspects, gas-phase AX and BY are prevented from mixing in the chamber by an appropriate purge and/or evacuation. In some aspects, BY may be chosen such that an A-B bond is favorable to the A-X bond, resulting in a formation of a layer or a partial layer of AB per cycle. For example, an exposure of trimethylaluminum (TMA) followed by a purge and/or evacuation purge of the process chamber and the introduction of an oxidizer such as (but not limited to) oxygen, water vapor, ozone, O*, nitrous oxide, nitric oxide, or hydrogen peroxide results in the formation of a controlled monolayer or a sub-monolayer of $Al_2O_3$. In some aspects, thickness is controlled by the number of cycles, where one cycle is defined as exposure to AX, purge (or evacuation/purge) and exposure to the BY and finally a purge (or evacuation/purge). Using proper dosing (time, temperature, pressure, and gas flow) during the ALD process, the precursor molecules may penetrate the pores of the device surfaces, including one or more electrodes, and diminish the pores and microcracks resulting in decreased leak rates.

In some instances, the precursor is AX, where A may be a metal and X may be a ligand which can be organic or halide ligand. AX may be, but is not limited to, trimethylaluminum (TMA), $AlCl_3$, $Al(CH_3)_3$, $Al(OC_2H_5)_3$, $Al(OCH_2CH_2CH_3)_3$, $Ir(acac)_3$, $(EtCp)Ir(COD)$, $IrF_6$, $MeCpPtMe_3$, $Pt(acac)_2$, $Ti(OC_2H_5)_4$, $Ti(OCH(CH_3)_2)_4$, $Ti(N(CH_3)_2)_4$, $Ti(N(C_2H_5)(CH_3))_4$, $TiCl_4$, $TiI_4$, $Zr(OC_2H_5)_4$, $ZrCl_4$, $ZrI_4$, $Ta(OC_2H_5)_5$, $Ta(Cl)_5$, $HfCl_4$, or any other precursor comprising a metal and an organic or halide ligand. In some instances, the precursor, BY, may be $O_2$, $NH_3$, $H_2O$, $N_2O$, $Cl_2$, $H_2O_2$, O*, or any other precursor. In some instances, layers are deposited in at least 1 cycle, 2 cycles, 3 cycles, 4 cycles, 5 cycles, 6 cycles, 7 cycles, 8 cycles, 9 cycles, 10 cycles, 11 cycles, 15 cycles, 20 cycles, 25 cycles, 50 cycles, 100 cycles, 500 cycles, or more.

In some instances, the temperature of an ALD system while the precursors are introduced is at least 10 degrees Celsius (° C.), 20° C., 50° C., 100° C., 120° C., 150° C., 180° C., 190° C., 200° C., 220° C., 250° C., 270° C., 300° C., 320° C., 350° C., 370° C., 400° C., or more. In some instances, the pressure of an ALD system during evacuation is at most 770 Torr, 500 Torr, 200 Torr, 100 Torr, 1E-1 Torr, 1E-2 Torr, 1E-3 Torr, 1E-4 Torr, 1E-5 Torr, 1E-6 Torr, 1E-7 Torr, 1E-8 Torr, 1E-9 Torr, 1E-10 Torr, or less. In some instances, the pressure of an ALD system during a purge is at least 1E-6 Torr, 1E-5 Torr, 1E-4 Torr, 1E-3 Torr, 1E-2 Torr, 1E-1 Torr, 1 Torr, 100 Torr, 300 Torr, 500 Torr, 800 Torr, or more. In some instances, the pressure of an ALD system during precursor exposure can be at least 1E-8 Torr, 1E-7 Torr, 1E-6 Torr, 1E-5 Torr, 1E-4 Torr, 1E-3 Torr, 1E-2 Torr, 1E-1 Torr, 1 Torr, 100 Torr, 200 Torr, 500 Torr, 700 Torr, 800 Torr, or more. In some instances, gas flow during ligand exposure is at least 1 standard cubic centimeters per minute (sccm), 10 sccm, 100 sccm, 1 standard liters per minute (slpm), 2 slpm, 5 slpm, 10 slpm, or more. In some instances, exposure time of a precursor in an ALD system is at least 1 millisecond, 10 milliseconds, 100 milliseconds, 1 seconds, 5 seconds(s), 10 s, 20 s, 30 s, 40 s, 50 s, 1 minute (min), 2 min, 3 min, 4 min, 5 min, 6 min, 7 min, 8 min, 9 min, 10 min, 15 min, or more.

ALD, or any other deposition method, may be used to seal or fill in microcracks or pores in a device or feedthrough. In some instances, the size of a microcrack or pore may be reduced by at least 1 percent (%), 2%, 3%, 4%, 5%, 10%, 25%, 50%, 75%, 100%, 200%, 300%, 400%, 500%, 600%, 700%, 800%, 900%, 1000%, 1200%, 1400%, 1600%, 2000%, or more. In some instances, the microcracks or pores are completely filled by a coating. When the size of a microcrack or pore is reduced using ALD, or any other deposition method, the leak rate through the microcrack or pore may be reduced, for example, by at least about 5%, 10%, 20%, 30%, 40%, 50%, 60%, 70%, 80%, 90%, 95%, or more.

In some instances, one or more coatings applied to a device may comprise a coating that (i) modifies one or more material properties of a device or (ii) provides a desired set of material properties for a device. In some cases, a plurality of coatings may be applied to the device. The plurality of coatings may comprise different coatings. In some cases, the plurality of coatings may be applied sequentially using different deposition techniques. The plurality of coatings may provide a combination of different material properties that can collectively enhance the biocompatibility and/or hermeticity of the device, or any portion or component thereof.

Figure 2A:
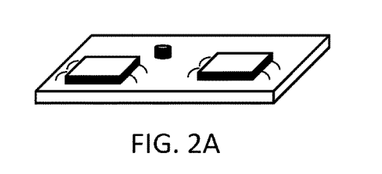
FIG. 2A illustrates an inner board or substrate with attached components.
Figure 2B:
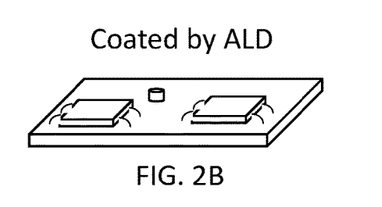
FIG. 2B illustrates an ALD coating of the inner components.
Figure 2C:
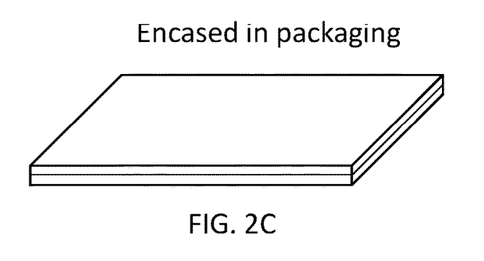
FIG. 2C illustrates the board or substrate encapsulated by housing.
Figure 2D:
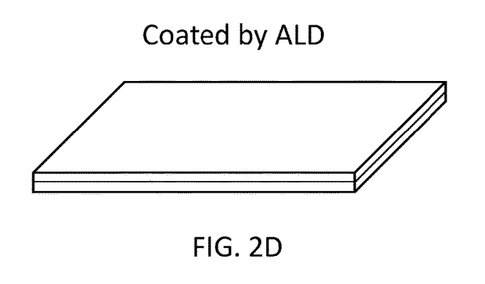
FIG. 2D illustrates the housing coated by ALD.

FIG. 2A illustrates an inner board (e.g., a circuit board) with attached components. FIG. 2B illustrates an ALD coating of the inner components. FIG. 2C illustrates the board encapsulated by housing. FIG. 2D illustrates the housing coated by ALD. ALD coatings may be applied to both outer and inner parts of the electronics (e.g., processors) of the device to protect sensitive components s well the encapsulation packaging. For example, a device may be coated to reduce interaction of undesirable materials with human body fluids in order to improve biostability and biocompatibility.

Figure 3A:
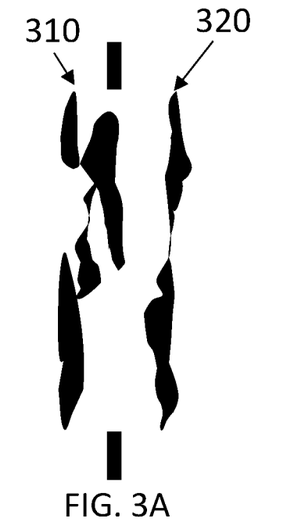
FIG. 3A illustrates a conducting feedthrough showing microcracks or pores.
Figure 3B:
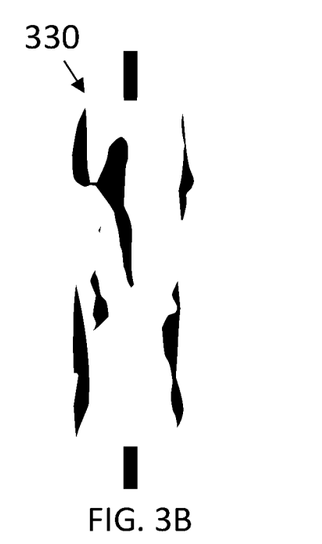
FIG. 3B illustrates sealed microcracks and pores.

FIG. 3A illustrates a conducting feedthrough showing microcracks 320 or pores 310. FIG. 3B illustrates sealed microcracks and pores 330. Such microcracks or pores are sealed using deposition methods like ALD, CVD, or any other method described herein. ALD may be particularly advantageous due to the surface reaction deposition which allow atoms and molecules to penetrate into micropores and cracks during the thin film deposition process. ALD may decrease the size of the pores and cracks and even seal them, and may be supplemented or complemented with another deposition method for large cracks and pores after ALD has first been used to seal smaller cracks and pores on the nanometer scale.

Material properties or desired set of material properties of a device may be hermeticity, biocompatibility, biostability, conductivity, resistivity, capacitance, inductance, electrical connectivity, electrical communication, corrosion resistance, robustness, structural design, delivery system, power management, detection, or wireless communication of the device, or any combination thereof. Material properties or a desired set of material properties may include shape, texture, or surface characteristics of a device or a portion thereof. A shape of a device or a portion thereof may be any shape, geometric or organic. A shape may be a circle, annulus, rectangle, or any other shape. A device or a portion thereof may be textured or patterned. For example, the device may comprise grooves, troughs, hills, and/or pillars. The device may define one or more cavities (e.g., micro-scale cavities or nano-scale cavities). The device may define one or more channels. The device may have regular textures and/or patterns across the surface of the device. For example, the device may have regular geometric structures (e.g., wedges, cuboids, cylinders, spheroids, hemispheres, etc.) above or below a reference level of the surface. Alternatively, the device may have irregular textures and/or patterns across the surface of the substrate. For example, the device may have any arbitrary structure above or below a reference level of the device. In some instances, a texture of the device may comprise structures having a maximum dimension of at most about 100%, 90%, 80%, 70%, 60%, 50%, 40%, 30%, 20%, 10%, 9%, 8%, 7%, 6%, 5%, 4%, 3%, 2%, 1%, 0.1%, 0.01%, 0.001%, 0.0001%, 0.00001% of the total thickness of the device wall. A device or a portion thereof may have surface characteristics. Surface characteristics may include surface roughness, hardness, corrosion resistance, or any other type of surface characteristic.

Hermeticity may be achieved by sealing a device, unit, or a portion thereof. The hermetically sealed unit may be manufactured as a single piece. The hermetically sealed unit may be packaged as a single piece. The one or more shanks may have a structural portion or region that forms at least a part of the one or more walls of the hermetically sealed unit. The hermetically sealed unit can be formed or manufactured without the use of any type of external fastener, for example. The hermetically sealed unit may be formed using an adhesive material or a welding process. In other cases, the hermetically sealed unit may be formed using a three-dimensional printing technique or method. The hermetically sealed unit may refer to a unit that prevents the ingress or passage of certain materials or fluids into or out of the hermetically sealed unit. The materials or fluids may have a particle size of at least about 2 Angstroms. The materials or fluids may have a particle size of at least about 2.5 Angstroms. The materials or fluids may have a particle size of at least about 3 Angstroms. The materials or fluids may have a particle size of at least about 1 nanometer. The materials or fluids may have a particle size of at least about 10 nanometers. The materials or fluids may have a particle size of at least about 100 nanometers. The materials or fluids may have a particle size of at least about 1 micrometer. The materials or fluids may have a particle size of at least about 10 micrometers. The materials or fluids may have a particle size of at least about 100 micrometers. The materials or fluids may have a particle size of at least about 1 millimeter. The materials or fluids may have a particle size of at least about 10 millimeters. In some cases, the materials or fluid may be a gas. In some cases, the materials or fluid may be a liquid.

In some cases, the hermetically sealed unit may comprise one wall, two walls, three walls, or any number of walls. Each wall may be substantially flat or substantially curved. Those skilled in the art will recognize that the at least one wall of the hermetically sealed unit may comprise many shapes, forms, and sizes without departing from the inventive concepts provided herein. In some instances, every surface of the device is hermetically sealed. In some instances, at least 10%, 20%, 30%, 40%, 50%, 60%, 70%, 80%, 90%, or 100% of the device is hermetically sealed. In some instances, only the electrode is hermetically sealed. In some instances only a portion of the electrode is hermetically sealed. In some instances, 100%, 90%, 80%, 70%, 60%, 50%, 40%, 30%, 20%, 10% or less of the electrode is hermetically sealed.

In some instances, at least the portion of a device comprises (i) one or more electronic components or circuits for processing one or more biological signals, or (ii) an inner or outer portion of a housing of a device, which housing contains one or more electronic components or circuits for processing one or more biological signals. A housing may be a chamber or an enclosure for the device, as described herein.

In some instances, the device comprises at least 1 electric component, 2, 3, 4, 5, 6, 7, 8, 9, 10, 15, 20, 25, 50, 70, 100, 200, 250, 300, 500, 1000, or more electric components. In some instances, the device comprises at least 1 circuit, 2, 3, 4, 5, 6, 7, 8, 9, 10, 15, 20, 25, 50, 70, 100, 200, 250, 300, 500, 1000, or more circuits.

In some instances, at least the portion of a device comprises one or more conducting feedthroughs of the device or a sealing material surrounding one or more conductive wires of the device. In some instances, a device may comprise at least 1 conducting feedthroughs of the device, 2, 3, 4, 5, 6, 7, 8, 9, 10, 15, 20, 25, 30, 50, 70, 80, 100, 200, 400, 1000 or more conducting feedthroughs of the device. In some instances, a scaling material surrounds at least 1 conductive wires of the device, 2, 3, 4, 5, 6, 7, 8, 9, 10, 15, 20, 25, 30, 50, 70, 80, 100, 200, 400, 1000 or more conductive wires of the device. A sealing material may be paper, rubber, silicone, metal, cork, felt, neoprene, nitrile rubber, fiberglass, polytetrafluoroethylene (PTFE), polychlorotrifluoroethylene, or any other sealing material known in the art.

In some instances, at least the portion of the device comprising one or more electrodes configured to transmit one or more biological signals from a tissue region of a subject to one or more electronic components or circuits of a device.

One or more coatings may be applied using a deposition technique to one or more electrodes to be used with a device. Coatings may be a conductive coating directly applied to one or more electrodes. Coatings may be an insulating coating directly applied to one or more electrode. Coatings may be insulating coatings applied on or to the conducting coating, or coatings may be conducting coatings applied on or to the insulating coating. Coatings may be selectively deposited on or applied to one or more select regions of the one or more electrodes. In some instances, one or more layers of coating is applied to cover 100% of an electrode surface. In some instances, 95%, 90%, 85%, 80%, 75%, 70%, 65%, 60%, 55%, 50%, 45%, 40%, 35%, 30%, 25%, 20%, 15%, 10%, 5%, or less surface of an electrode is coated. In some instances, the entire electrode is coated or the entire electrode except the tip of the electrode is coated. A tip of an electrode may be at least 0.1% of the total electrode length, 0.5%, 1%, 2%, 3%, 4%, 5%, 6%, 7%, 8%, 9%, 10%, 12%, 15%, 20%, or more of total electrode length.

In some instances, the method may comprise, prior to (b) masking one or more select regions of one or more electrodes.

In some instances, the method may comprise, in (b), applying one or more coatings by applying a plurality of repeatable layers of a film material or a nanolaminate to a device or a portion thereof. Repeatable layers may be ternary layers (e.g., $Al_xHf_yO_z$ which is a mixture of $Al_2O_3$ and $HfO_2$). As discussed elsewhere herein, the ternary layer material may comprise, for example, any compound or composition that can be represented as $A_xB_yC_z$, where A, B, and C are derived from or associated with a compound or composition AC and/or BC. In some embodiments, A and/or B may comprise, for example, a metal, a metal alloy, and/or any non-metallic element or material. In some embodiments, C may comprise one or more oxides, nitrides, carbides, metals, or metal alloys. In some cases, the metal or metal alloy may comprise, for instance, platinum or platinum iridium. In some non-limiting embodiments, and by way of example only, the ternary layer material may comprise a combination of two binary oxides. In some non-limiting embodiments, and by way of example only, the ternary layer material may comprise $Al_xHf_yO_z$. In some instances, at least 1 coat, 2 coats, 3 coats, 4 coats, 5 coats, 6 coats, 7 coats, 8 coats, 9 coats, 10 coats, 11 coats, 12 coats, 13 coats, 14 coats, 15 coats, 20 coats, or more may be applied. Layers may comprise an identical film or nanolaminate material. In some instances, different film material or nanolaminate can comprise the layers. For example, one layer may comprise of a first film material and a second layer may comprise of a second film material, where the first and second film material are different. Likewise, one layer may comprise a first nanolaminate and second layer may comprise a second nanolaminate, where the first and second nanolaminate are different. Similarly, one layer may comprise a nanolaminate and second layer may comprise a film material. Films and nanolaminates may be differentiated according to thickness. For example, a nanolaminate is a sub-category of a thin film, where the thickness of the film is less than 100 nanometers (nm). A film, on the other hand, is greater than 100 nm in thickness. In some instances, a film may be up to 50 micrometers in thickness. In any of the embodiments described herein, the coatings, films, and/or stabilizing materials may comprise a metal, a metal alloy, or a non-metal.

In some instances, the method may comprise, subsequent to (b), exposing at least a portion of the one or more electrodes to enable detection and/or transmission of the one or more biological signals. Electrode surfaces may be exposed 0%, 0.5%, 1%, 2%, 3%, 4%, 5%, 6%, 7%, 8%, 9%, 10%, 12%, 15%, 20%, or more. Electrodes may be exposed by ablating at least one or more coatings of the electrode. Electrodes may be exposed through ablation methods like laser ablation, photoablation, electro-ablation, vaporization, sublimation, calving chipping, chemical etching, or any other erosive process known in the art. Electrodes may be exposed by physically and/or chemically removing at least one or more coatings. In some instances, one or more coatings comprise a coating that acts as an etch stop layer to chemically or physically resist etching in or near one or more select areas or regions of one or more electrodes.

In an example, electrodes may be exposed through laser ablation methods. A laser ablation system may be configured to direct a laser to a target area of an electrode, where the electrode may comprise one or more coatings. In some instances, one or more coatings may be resistive towards laser ablation.

A system for laser ablation may comprise one or more lasers. The one or more lasers may comprise lasers of different types and may include any laser that produces laser beams or pulses with wavelengths within the ultraviolet, visible, or infrared spectrum. The one or more lasers may be configured to operate in either a continuous wave mode or a pulsed mode to provide pulses that are at least about 1 femtosecond or greater. In some cases, the one or more lasers may comprise excimer lasers that can produce high-energy nanosecond-scale pulses of light with wavelengths within the ultraviolet spectrum and ablate one or more layers of a coating without compromising the electrode. In some cases, the one or more lasers may comprise infrared lasers and/or femtosecond lasers. The wavelengths of the laser beams or the laser pulses generated by the one or more lasers may range from about 193 nanometers (nm) to about 1200 nm, while pulse durations may range from about 1 picosecond (ps) to about 10 microseconds (μs).

In some cases, the laser of a laser ablation system may be a solid-state laser, a gas laser, a liquid laser, or a semiconductor laser. A solid-state laser may be a laser that uses a solid material (e.g., glass or a crystalline material) as a laser medium. The solid-state laser may be a ruby laser, a Nd:YAG laser, a NdCrYAG laser, an Er:YAG laser, a neodymium YLF (Nd:YLF) solid-state laser, a neodymium doped Yttrium orthovanadate (Nd:YVO4) laser, a neodymium doped yttrium calcium oxoborate Nd:YCa4O (BO3)3 (Nd:YCOB) laser, a neodymium glass (Nd:Glass) laser, a titanium sapphire (Ti:sapphire) laser, a thulium YAG(Tm:YAG) laser, a ytterbium YAG (Yb:YAG) laser, a ytterbium: 2O3 (glass or ceramics) laser, a ytterbium doped glass laser (rod, plate/chip, and fiber), a holmium YAG (Ho:YAG) laser, a chromium ZnSe(Cr:ZnSe) laser, a cerium doped lithium strontium (or calcium) aluminum fluoride (Ce:LiSAF, Ce:LiCAF) laser, a promethium 147 doped phosphate glass solid-state laser, a chromium doped chrysoberyl(alexandrite) laser, an erbium doped laser, an erbium-ytterbium co-doped glass laser, a trivalent uranium doped calcium fluoride (U:CaF2) solid-state laser, a divalent samarium doped calcium fluoride (Sm:CaF2) laser, and/or an F-Center laser. A gas laser may be a laser in which an electric current is discharged through a gas inside a laser medium to produce laser light. The gas laser may be an argon laser, a carbon dioxide laser, a carbon monoxide laser, an excimer laser, a helium laser, a helium-neon laser, a krypton laser, a nitrogen laser, or a xenon laser. A liquid laser may be a laser that uses a liquid as laser medium. In some cases, the liquid laser may be a dye laser. Dye lasers may use different organic dyes to produce emissions from the ultraviolet to near infrared spectrum. Dye lasers may be operated in the visible with tunable emissions of red, yellow, green, or blue laser emission at almost any wavelength. The dye laser may use Rhodamine-6G in solution. A semiconductor laser may be a laser that uses a p-n junction of a semiconductor diode as the laser medium. The semiconductor laser may be a semiconductor laser diode, a GaN laser, an InGaN laser, an AlGaInP, an AlGaAs, an InGaAsP, a lead salt laser, a vertical cavity surface emitting laser (VCSEL), a quantum cascade laser, and/or a hybrid silicon laser.

In some cases, the laser of a laser ablation system may be a chemical laser. A chemical laser may include a hydrogen fluoride laser, a deuterium fluoride laser, a chemical oxygen-iodine laser, or an all gas-phase iodine laser. In other cases, the laser may be a metal-vapor laser. The metal-vapor laser may be a helium-cadmium (HeCd) metal-vapor laser, a helium-mercury (HeHg) metal-vapor laser, a helium-selenium (HeSe) metal-vapor laser, a helium-silver (HeAg) metal-vapor laser, a strontium vapor laser, a neon-copper (NeCu) metal-vapor laser, a copper vapor laser, a gold vapor laser, and/or a manganese (Mn/MnCl2) vapor laser. Alternatively, the laser may be a free electron laser, a gas dynamic laser, a Samarium laser, a Raman laser, and/or a nuclear pumped laser.

The laser of a laser ablation system may be configured to operate as a continuous wave laser, a single pulsed laser, a Q-switched laser, a repetitively pulsed laser, and/or a mode locked laser.

In some cases, the laser of a laser ablation system may be configured to emit a plurality of pulses. The plurality of pulses may have a pulse energy of between 0.01 microjoules ($\mu$J) and 1 joule (J). The plurality of pulses may comprise one or more laser pulses with a wavelength of between about 100 nm and about 4000 nm. In some cases, the wavelength may be at least about 100 nm, 200 nm, 300 nm, 400 nm, 500 nm, 600 nm, 700 nm, 800 nm, 900 nm, 1000 nm, 2000 nm, 3000 nm, 4000 nm, or more. In some cases, the wavelength may be at most about 4000 nm, 3000 nm, 2000 nm, 1000 nm, 900 nm, 800 nm, 700 nm, 600 nm, 500 nm, 400 nm, 300 nm, 200 nm, 100 nm, or less.

In some instances, the one or more pulses emitted by the laser of a laser ablation system may have a pulse duration or a pulse width. The pulse duration may range from about 1 femtosecond to about 1 second. In some cases, the laser may be configured to emit one or more pulses at a predetermined pulse repetition frequency (PRF). The PRF may range between 1 Hz to 100 MHz. In some cases, the one or more pulses emitted by the laser may have a pulse energy density. The pulse energy density may range from about 1 $\mu$J/cm$^2$ to about 100 J/cm$^2$. The laser may have an average power. The average power may range from about 0.1 milliwatts (mW) to about 1 Watt (W). The laser beam may have a beam spot size. The beam spot size may range from about 0.001 mm to about 1 cm. In some instances, the laser may be configured to ablate a surface or a portion of the dura mater, the arachnoid mater, and/or the pia mater in a manner such that the laser achieves a penetration depth of between about 0.01 mm to about 1 cm. In some instances, one or more properties (e.g., mode of operation, pulse energy, wavelength, pulse duration, pulse width, pulse repetition frequency, pulse energy density, average power, beam spot size, etc.) of the laser may be adjusted to achieve a desired penetration depth during laser ablation and/or to achieve a desired rate of photoablation.

In some cases, a mask, or a resist, may be used to protect one or more electrodes from damage due to laser pulses while performing laser ablation. The mask may comprise of a number of different materials. These can include a metallic material, a polymeric material, a ceramic material, and/or any other composite solid material. The mask may comprise a metal mask, a ceramic mask, or a polymer mask. In some examples, aluminum, stainless steel, titanium nickel or tungsten may be used for metal masks. In some cases, ceramic masks may comprise silicon, glass that is opaque to the utilized wavelength but transparent to visible light, and/or sapphire. In some cases, polymer masks may comprise polypropylene, polyethylene, one or more fluoropolymers, one or more polyimides, a hydrogel, and/or silicone. In some cases, the polymer masks may comprise a material that is opaque to ultraviolet (UV) or infrared (IR) light but transparent to light in the visible spectrum. In some cases, the mask may comprise a liquid or gel such as Vaseline, which may be applied through a stencil or directly on the surface of the electrode. The applied liquid or gel may harden to form a solid. Methods for generating masks and stencils include, but are not limited to, three-dimensional (3D) printing, machining, stamping, extrusion, casting, and/or molding. The mask or stencil shape may be produced or manufactured using any of the above mentioned methods (e.g., three-dimensional (3D) printing, machining, stamping, extrusion, casting, and/or molding).

As described above, in some cases the mask may comprise a metallic material. The metallic material may comprise one or more elements selected from the group consisting of aluminum, platinum, calcium, magnesium, barium, scandium, titanium, vanadium, chromium, manganese, iron, cobalt, nickel, copper, zinc, yttrium, niobium, molybdenum, ruthenium, rhodium, silver, cadmium, actinium, and gold. In some cases, the metallic material may comprise an intermetallic material. The intermetallic material may be a solid-state compound exhibiting metallic bonding, defined stoichiometry and ordered crystal structure (i.e., alloys). The intermetallic material may be in a prealloyed powder form. Examples of such prealloyed powders may include, but are not limited to, brass (copper and zinc), bronze (copper and tin), duralumin (aluminum, copper, manganese, and/or magnesium), gold alloys (gold and copper), rose-gold alloys (gold, copper, and zinc), nichrome (nickel and chromium), and/or stainless steel (iron, carbon, and additional elements including manganese, nickel, chromium, molybdenum, boron, titanium, silicon, vanadium, tungsten, cobalt, and/or niobium). In some cases, the prealloyed powders may include superalloys. The superalloys may comprise iron, nickel, cobalt, chromium, tungsten, molybdenum, tantalum, niobium, titanium, and/or aluminum.

As described above, in some cases the mask may comprise a polymeric material. The polymeric material may comprise one or more polymers. The one or more polymers may comprise monomers to be polymerized into the one or more polymers, oligomers to be cross-linked into the one or more polymers, or both. The monomers may be of the same or different types. An oligomer may comprise two or more monomers that are covalently linked to each other. The oligomer may be of any length, such as at least 2 (dimer), 3 (trimer), 4 (tetramer), 5 (pentamer), 6 (hexamer), 7, 8, 9, 10, 20, 30, 40, 50, 100, 200, 300, 400, 500, or more monomers. In some cases, the one or more polymers may comprise a homopolymer and/or a copolymer. The homopolymer may comprise one or more identical monomer units. The copolymer may be a linear copolymer or a branched copolymer. The copolymer may be an alternating copolymer, periodic copolymer, statistical copolymer, random copolymer, and/or block copolymer. Examples of monomers may include one or more of hydroxyethyl methacrylate; n-Lauryl acrylate; tetrahydrofurfuryl methacrylate; 2,2,2-trifluoroethyl methacrylate; isobornyl methacrylate; polypropylene glycol monomethacrylates, aliphatic urethane acrylate (i.e., Rahn Genomer 1122); hydroxyethyl acrylate; n-Lauryl methacrylate; tetrahydrofurfuryl acrylate; 2,2,2-trifluoroethyl acrylate; isobornyl acrylate; polypropylene glycol monoacrylates; trimethylpropane triacrylate; trimethylpropane trimethacrylate; pentaerythritol tetraacrylate; pentaerythritol tetraacrylate; triethyleneglycol diacrylate; triethylene glycol dimethacrylate; tetrathyleneglycol diacrylate; tetrathylene glycol dimethacrylate; neopentyldimethacrylate; neopentylacrylate; hexane dioldimethacrylate; hexane diol diacrylate; polyethylene glycol 400 dimethacrylate; polyethylene glycol 400 diacrylate; diethylglycol diacrylate; diethylene glycol dimethacrylate; ethyleneglycol diacrylate; ethylene glycol dimethacrylate; ethoxylated bis phenol A dimethacrylate; ethoxylated bis phenol A diacrylate; bisphenol A glycidyl methacrylate; bisphenol A glycidyl acrylate; ditrimethylolpropane tetraacrylate; and ditrimethylolpropane tetraacrylate.

As described above, in some cases the mask may comprise a ceramic material. The ceramic material may comprise metal (e.g., aluminum, platinum, titanium, etc.), non-metal (e.g., oxygen, nitrogen, etc.), and/or metalloid (e.g., germanium, silicon, etc.) atoms primarily held in ionic and/or covalent bonds. A metal may be any element selected from the group consisting of aluminum, platinum, calcium, magnesium, barium, scandium, titanium, vanadium, chromium, manganese, iron, cobalt, nickel, copper, zinc, yttrium, niobium, molybdenum, ruthenium, rhodium, silver, cadmium, actinium, and gold. A non-metal may be any element selected from the group consisting of hydrogen, carbon, nitrogen, oxygen, phosphorus, sulfur, selenium, fluorine, chlorine, bromine, iodine, astatine, tennessine, helium, neon, argon, krypton, xenon, radon, and oganesson. A metalloid may be any element selected from the group consisting of arsenic, tellurium, germanium, silicon, antimony, boron, polonium, astatine, and selenium. In some cases, the ceramic material may be, for example, aluminide, boride, beryllia, carbide, chromium oxide, hydroxide, sulfide, nitride, mullite, kyanite, ferrite, titania zirconia, yttria, and/or magnesia.

As described above, in some cases the mask may comprise one or more composite materials. The one or more composite materials may comprise fiberglass, carbon fibers, carbon nanofibers, fiber-reinforced polymers, carbon-fiber-reinforced polymers, or glass-reinforced plastics.

In some cases, the mask may comprise a liquid or a gel such as Vaseline, which may be applied through a stencil or directly on the surface of the ablation site. In some cases, the applied liquid may harden to form a solid.

In an example, electrodes may be exposed through chemical etching methods. An etchant may be in the form a plasma, solid, liquid, or gas. An etchant may be configured to directly react with a target area of an electrode, where the electrode may comprise one or more coatings. In some instances, one or more coatings may be resistive towards chemical etching. An electrode may be exposed to an etchant at least 1 once, twice, thrice, four times, five times, six times, seven times, 10 times, 15 times, or more.

Etchants may be sodium hydroxide, keller's reagent, hydrochloric acid, nitric acid, ferric chloride, Nital, copper chloride, ammonium persulfate, ammonia, hydrogen peroxide, hydrofluoric acid, phosphoric acid, sulfuric acid, iodic acid, hydrobromic acid, perchloric acid, Adler's reagent, or any other etchant known in the art. An etchant solution may be at least 0.000001 moles per liter (M), 0.00001 M, 0.0001 M, 0.001 M, 0.01 M, 0.1 M, 0.5 M, 1.0 M, 2.0 M, 3.0 M, 4.0 M, 5.0 M, 6.0 M, 7.0 M, 8.0 M, 9.0 M, 10.0 M, 11.0 M, 12.0 M, 13.0 M, 14.0 M, 15.0 M, 16.0 M, 17.0 M, 18.0 M, 19.0 M, 20.0 M, 25.0 M, or more concentrated.

In some cases, a mask, or a resist, may be used to protect one or more electrodes from damage due to chemical etching. The mask may comprise of a number of different materials. These can include a metallic material, a polymeric material, a ceramic material, and/or any other composite solid material. The mask may comprise a metal mask, a ceramic mask, or a polymer mask. In some examples, aluminum, stainless steel, titanium nickel or tungsten may be used for metal masks. In some cases, ceramic masks may comprise silicon, glass that is opaque to the utilized wavelength but transparent to visible light, and/or sapphire. In some cases, polymer masks may comprise polypropylene, polyethylene, one or more fluoropolymers, one or more polyimides, a hydrogel, and/or silicone. In some cases, the polymer masks may comprise a material that is opaque to ultraviolet (UV) or infrared (IR) light but transparent to light in the visible spectrum. In some cases, the mask may comprise a liquid or gel such as Vaseline, which may be applied through a stencil or directly on the surface of the electrode. The applied liquid or gel may harden to form a solid. Methods for generating masks and stencils include, but are not limited to, three-dimensional (3D) printing, machining, stamping, extrusion, casting, and/or molding. The mask or stencil shape may be produced or manufactured using any of the above-mentioned methods (e.g., three-dimensional (3D) printing, machining, stamping, extrusion, casting, and/or molding).

As described above, in some cases the mask may comprise a metallic material. The metallic material may comprise one or more elements selected from the group consisting of aluminum, platinum, calcium, magnesium, barium, scandium, titanium, vanadium, chromium, manganese, iron, cobalt, nickel, copper, zinc, yttrium, niobium, molybdenum, ruthenium, rhodium, silver, cadmium, actinium, and gold. In some cases, the metallic material may comprise an intermetallic material. The intermetallic material may be a solid-state compound exhibiting metallic bonding, defined stoichiometry and ordered crystal structure (i.e., alloys). The intermetallic material may be in a prealloyed powder form. Examples of such prealloyed powders may include, but are not limited to, brass (copper and zinc), bronze (copper and tin), duralumin (aluminum, copper, manganese, and/or magnesium), gold alloys (gold and copper), rose-gold alloys (gold, copper, and zinc), nichrome (nickel and chromium), and/or stainless steel (iron, carbon, and additional elements including manganese, nickel, chromium, molybdenum, boron, titanium, silicon, vanadium, tungsten, cobalt, and/or niobium). In some cases, the prealloyed powders may include superalloys. The superalloys may comprise iron, nickel, cobalt, chromium, tungsten, molybdenum, tantalum, niobium, titanium, and/or aluminum.

As described above, in some cases the mask may comprise a polymeric material. The polymeric material may comprise one or more polymers. The one or more polymers may comprise monomers to be polymerized into the one or more polymers, oligomers to be cross-linked into the one or more polymers, or both. The monomers may be of the same or different types. An oligomer may comprise two or more monomers that are covalently linked to each other. The oligomer may be of any length, such as at least 2 (dimer), 3 (trimer), 4 (tetramer), 5 (pentamer), 6 (hexamer), 7, 8, 9, 10, 20, 30, 40, 50, 100, 200, 300, 400, 500, or more monomers. In some cases, the one or more polymers may comprise a homopolymer and/or a copolymer. The homopolymer may comprise one or more identical monomer units. The copolymer may be a linear copolymer or a branched copolymer. The copolymer may be an alternating copolymer, periodic copolymer, statistical copolymer, random copolymer, and/or block copolymer. Examples of monomers may include one or more of hydroxyethyl methacrylate; n-Lauryl acrylate; tetrahydrofurfuryl methacrylate; 2,2,2-trifluoroethyl methacrylate; isobornyl methacrylate; polypropylene glycol monomethacrylates, aliphatic urethane acrylate (i.e., Rahn Genomer 1122); hydroxyethyl acrylate; n-Lauryl methacrylate; tetrahydrofurfuryl acrylate; 2,2,2-trifluoroethyl acrylate; isobornyl acrylate; polypropylene glycol monoacrylates; trimethylpropane triacrylate; trimethylpropane trimethacrylate; pentaerythritol tetraacrylate; pentaerythritol tetraacrylate; triethyleneglycol diacrylate; triethylene glycol dimethacrylate; tetrathyleneglycol diacrylate; tetrathylene glycol dimethacrylate; neopentyldimethacrylate; neopentylacrylate; hexane dioldimethacylate; hexane diol diacrylate; polyethylene glycol 400 dimethacrylate; polyethylene glycol 400 diacrylate; diethylglycol diacrylate; diethylene glycol dimethacrylate; ethyleneglycol diacrylate; ethylene glycol dimethacrylate; ethoxylated bis phenol A dimethacrylate; ethoxylated bis phenol A diacrylate; bisphenol A glycidyl methacrylate; bisphenol A glycidyl acrylate; ditrimethylolpropane tetraacrylate; and ditrimethylolpropane tetraacrylate.

As described above, in some cases the mask may comprise a ceramic material. The ceramic material may comprise metal (e.g., aluminum, platinum, titanium, etc.), non-metal (e.g., oxygen, nitrogen, etc.), and/or metalloid (e.g., germanium, silicon, etc.) atoms primarily held in ionic and/or covalent bonds. A metal may be any element selected from the group consisting of aluminum, platinum, calcium, magnesium, barium, scandium, titanium, vanadium, chromium, manganese, iron, cobalt, nickel, copper, zinc, yttrium, niobium, molybdenum, ruthenium, rhodium, silver, cadmium, actinium, and gold. A non-metal may be any element selected from the group consisting of hydrogen, carbon, nitrogen, oxygen, phosphorus, sulfur, selenium, fluorine, chlorine, bromine, iodine, astatine, tennessine, helium, neon, argon, krypton, xenon, radon, and oganesson. A metalloid may be any element selected from the group consisting of arsenic, tellurium, germanium, silicon, antimony, boron, polonium, astatine, and selenium. In some cases, the ceramic material may be, for example, aluminide, boride, beryllia, carbide, chromium oxide, hydroxide, sulfide, nitride, mullite, kyanite, ferrite, titania zirconia, yttria, and/or magnesia.

As described above, in some cases the mask may comprise one or more composite materials. The one or more composite materials may comprise fiberglass, carbon fibers, carbon nanofibers, fiber-reinforced polymers, carbon-fiber-reinforced polymers, or glass-reinforced plastics.

In some cases, the mask may comprise a liquid or a gel such as Vaseline, which may be applied through a stencil or directly on the surface of the ablation site. In some cases, the applied liquid may harden to form a solid.

In some instances, the mask, or resist, may be removed from the electrode subsequent to exposing electrode to an etchant one or times.

Coatings applied to a device or electrode may reflect or mitigate laser light to control (i) an absorption of laser energy or (ii) a thermal dissipation of absorbed laser energy for one or more select areas or regions of one or more electrodes. Coatings may mitigate chemical etching to control a reaction between an etchant and coating. Coatings may be hydrophobic, hydrophilic, or a combination thereof. In some instances, a region of an electrode coatings will be hydrophobic while a second region of an electrode coating will be hydrophilic. In some instances, one or more electrode coatings may be hydrophobic, hydrophilic, or a combination thereof. In some instances, coatings will have a contact angle with water of at least 80 degrees) (°), 90°, 100°, 110°, 120°, 130°, 140°, 150°, 160°, 170°, 180°, or more. In some instances, coatings will have a contact angle with water of at most 80°, 70°, 60°, 50°, 40°, 30°, 20°, 10°, 5°, or less. Coatings may be applied to one or more electrodes using one or more deposition techniques. Deposition techniques may be atomic layer deposition (ALD), chemical vapor deposition (CVD), physical vapor deposition (PVD), electroplating, plasma enhanced CVD, low pressure CVD, spin coating, sputtering, molecular beam epitaxy (MBE), molecule layer deposition, Langmuir-Blodgett method, chemical solution deposition (CSD), chemical bath deposition (CBD), sol-gel method, dip coating, thermal evaporation, pulsed laser deposition, cathodic arc deposition, ion beam deposition, electrospray deposition, electroplating, metalorganic vapor phase epitaxy (MOVPE), metalorganic CVD, or any combination thereof. In some instances, the electrodes may be coated with a low-impedance coating, such as iridium oxide (or any other transition-metal oxide, such as MnO2, rare-earth-metal oxide, such as $CeO_2$, main-group-metal oxide, such as $Bi_2O_3$ etc.), a conductive polymer (e.g., poly(3,4-ethylenedioxythiophene (PEDOT), etc.), a metal (e.g., Cu, etc), mineral silicates, metal fluorides, metal carbonates, hydrocarbons, powdered metal alloys with a binder, or a material promoting a high surface area (e.g. carbon nanotubes, platinum black, nanoparticle composites, metal organic frameworks, organic frameworks, and the like). A metal can be an alkali metal, an alkaline earth metal, a transition metal, a main group metal, a lanthanide metal, or an actinide metal. In some examples, coatings may comprise metal oxides, metal nitrides, metal carbides, and metal films or alloys. Coatings may comprise Al2O3, ZnO, TiO2, SiO2, HfO2, ZrO2, TIN, TION, Fe2O3, Ta2O5, TaN, Ti, Pt, Co, Cr, Mo, Ni, Li, Ir, Ta, Nb, Pd, Sn, Fe, NbO, NbO2, Nb2O5, W, WO3, AlN, TiN, WN, IrO2, WC, diamond like carbon, Calcium phosphate, Ca—P—O, or any other metal oxide, metal nitride, metal carbide, metal films, or alloys. In some examples one or more coatings may comprise the same material or different materials.

Figure 4A:
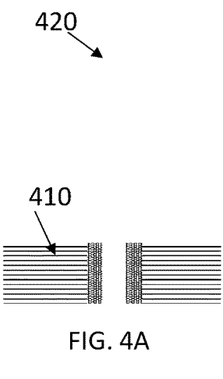
FIG. 4A illustrates an electrode.
Figure 4B:
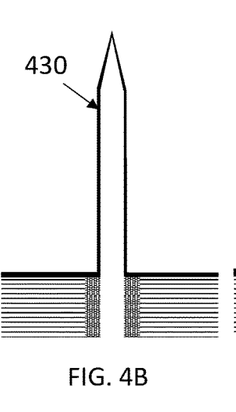
FIG. 4B and FIG. 4C illustrate one or more coatings applied to an electrode.
Figure 4C:
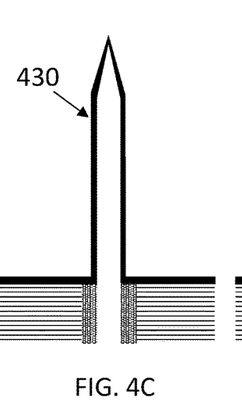
Figure 4D:
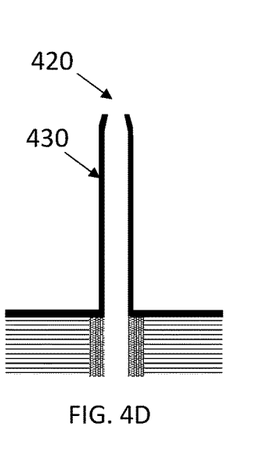
FIG. 4D illustrates an exposed electrode tip.

FIG. 4A illustrates a full exposed electrode 420 embedded in a feedthrough 410. FIG. 4B illustrates one coating 430 applied to an electrode while FIG. 4C illustrates multiple coatings 430 applied to an electrode. FIG. 4D illustrates an exposed electrode tip 420. These electrodes may be generated using the methods described herein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method, comprising:
   a. providing a device that is (i) implantable in a tissue region of a subject and (ii) configured to detect or measure one or more biological signals from the tissue region;
   b. applying one or more coatings to the device using at least atomic layer deposition to (i) seal one or more microcracks or pores in at least a portion of the device or (ii) reduce a size of the one or more microcracks or pores, thereby enhancing the hermeticity of the device; and
   c. implanting the device in the tissue region of the subject to detect or measure the one or more biological signals of the subject, wherein at least a portion of the device comprises one or more electrodes configured to transmit the one or more biological signals from the tissue region of the subject to one or more electronic components or circuits of the device.

2. The method of claim 1, wherein the one or more coatings comprise a coating that (i) modifies one or more material properties of the device or (ii) provides a desired set of material properties for the device.

3. The method of claim 2, wherein the one or more material properties or the desired set of material properties, or both comprise hermeticity, biocompatibility, or biostability of the device, or one or more electrical properties selected from the group consisting of conductivity, resistivity, capacitance, and inductance.

4. The method of claim 2, wherein the one or more material properties or the desired set of material properties, or both comprise a shape, a texture, or a surface characteristic of the device or a portion thereof.

5. The method of claim 1, wherein at least a portion of the device comprises an inner or outer portion of a housing of the device, and wherein the housing of the device contains the one or more electronic components or circuits for processing the one or more biological signals.

6. The method of claim 1, wherein at least a portion of the device comprises one or more conducting feedthroughs of the device or a sealing material surrounding one or more conductive wires of the device.

7. The method of claim 1, wherein the one or more coatings comprise (i) a conductive coating directly applied to the one or more electrodes and (ii) an insulating coating applied to the conducting coating.

8. The method of claim 1, wherein the one or more coatings are selectively of applied to one or more select regions of the one or more electrodes.

9. The method of claim 1, further comprising, prior to (b), masking one or more select regions of the one or more electrodes.

10. The method of claim 1, further comprising, subsequent to (b), exposing at least a portion of the one or more electrodes to enable detection or transmission, or both of the one or more biological signals.

11. The method of claim 10, wherein the exposing at least the portion of the one or more electrodes comprises ablating at least one coating of the one or more coatings.

12. The method of claim 11, wherein the one or more coatings comprise a coating that reflects or mitigates laser light to control (i) an absorption of laser energy or (ii) a thermal dissipation of absorbed laser energy for one or more select areas or regions of the one or more electrodes.

13. The method of claim 10, wherein the exposing at least the portion of the one or more electrodes comprises chemically etching at least one coating of the one or more coatings.

14. The method of claim 13, wherein the one or more coatings comprise a coating that acts as an etch stop layer to chemically resist etching in or near one or more select areas or regions of the one or more electrodes.

15. The method of claim 1, wherein at least one coating of the one or more coatings is hydrophobic.

16. The method of claim 1, wherein the one or more coatings comprise a plurality of coatings that are applied using different deposition techniques.

17. The method of claim 16, wherein the different deposition techniques are selected from a group consisting of chemical vapor deposition, physical vapor deposition, electroplating, plasma enhanced chemical vapor deposition, low pressure chemical vapor deposition, and atomic layer deposition.

18. The method of claim 1, wherein the one or more coatings comprise metal oxides, metal nitrides, metal carbides and metal films or alloys such as $Al_2O_3$, $ZnO$, $TiO_2$, $SiO_2$, $HfO_2$, $ZrO_2$, $TiN$, $TiON$, $Fe_2O_3$, $Ta_2O_5$, $TaN$, $Ti$, $Pt$, $Co$, $Cr$, $Mo$, $Ni$, $Li$, $Ir$, $Ta$, $Nb$, $Pd$, $Sn$, $Fe$, $NbO$, $NbO_2$, $Nb_2O_5$, $W$, $WO_3$, $AlN$, $TiN$, $WN$, $IrO_2$, $WC$, diamond like carbon, Calcium phosphate or Ca—P—O.

19. The method of claim 1, wherein in (b), applying the one or more coatings comprises applying a plurality of repeatable layers of a film material, a nanolaminate, or a ternary layer material to the device or a portion thereof.

20. The method of claim 19, wherein the ternary layer material comprises $Al_xHf_yO_z$.

* * * * *